United States Patent [19]

Ogawa et al.

[11] Patent Number: 4,837,371

[45] Date of Patent: Jun. 6, 1989

[54] PROCESS FOR CONCENTRATION OF AN AQUEOUS SOLUTION OF AMINO ACID

[75] Inventors: Shinji Ogawa, Kanagawa; Seiya Iguchi, Tokyo; Hiroshi Kimura; Yoh Ohmori, both of Kanagawa, all of Japan

[73] Assignee: Mitsui Toatsu Chemicals, Inc., Tokyo, Japan

[21] Appl. No.: 92,442

[22] Filed: Sep. 3, 1987

[30] Foreign Application Priority Data

Sep. 8, 1986 [JP] Japan .................................. 61-209621

[51] Int. Cl.$^4$ ...................... C07D 209/20; C07C 99/12
[52] U.S. Cl. .................................... 548/497; 548/496; 548/344; 562/445; 562/554; 562/557; 562/559
[58] Field of Search ................ 548/497; 562/554, 557, 562/559, 445

[56] References Cited

U.S. PATENT DOCUMENTS 2,471,053  5/1986  Almquist et al. .................... 562/554
4,601,829  7/1986  Kameko et al. ...................... 548/497

FOREIGN PATENT DOCUMENTS 0156513  10/1985  European Pat. Off. ............ 548/497
152355   8/1984  Japan .

Primary Examiner—David B. Springer
Attorney, Agent, or Firm—Albert L. Jeffers; Lawrence A. Steward

[57] ABSTRACT

An aqueous solution containing amino acids of which the solubility in water at isoelectric point is low, can be highly concentrated by means of semipermeable membranes in the presence of a water-soluble organic solvent while increasing the solubility by adjusting a pH.

1 Claim, 2 Drawing Sheets

PROCESS FOR CONCENTRATION OF AN AQUEOUS SOLUTION OF AMINO ACID

BACKGROUND OF THE INVENTION (i) Field of the Invention:

This invention relates to a process for concentration of an aqueous solution of amino acid and particularly, to a process for concentrating amino acids having a low solubility in water at isoelectric point by means of semipermeable membranes.

(ii) Description of the Prior Art:

Reverse osmosis membranes (hereinafter referred to as "RO membranes") are applicable to the recovery and concentration of end materials in a solution at temperatures near to room temperature without bringing about a phase change.

The concentration process using RO membranes which has many advantages such as less energy consumption is recently attracting attention and finding its uses in a variety of fields. A typical example of the use is the separation of extremely low molecular weight solutes exemplified by inorganic salts. The recent diversified uses owe to the development of composite RO membranes having a good heat and solvent resistance and "loose" RO membranes resembling ultrafiltration membranes which permit the passage of extremely low molecular weight solutes.

A prospective application area of RO membranes is the separation and purification of amino acids from dilute aqueous solutions produced by fermentation, chemical synthesis, or enzymatic synthesis, which is carried out by crystallization, ion-exchange, electrodialysis, or solvent extraction at the present time.

In these processes for concentration there are, in many cases, used means consuming a great deal of heat energy such as concentration method by heat evaporation and multiple effect evaporators. Accordingly, if the concentration process using the RO membrane is applicable to the concentration of an aqueous solution of amino acid, it can be highly expected as a concentration process of less energy consumption.

It is expected that the RO membrane, which can be applied to solutions containing no suspending solids owing to the principle, will be able to concentrate a dilute aqueous solution of an amino acid, such as proline, arginine, lysine, sodium glutamate, serine, and glycine which are all highly soluble in water, up to high concentrations even at the isoelectric point of the amino acids. In actual, a working example of such use of RO membranes is reported in, for example, Japanese Patent Laid-open No. 152355/1984. However, RO membranes cannot concentrate to high concentrations the aqueous solutions of aromatic ring-containing amino acids such as tryptophan, tyrosine, and phenylalanine and sulfur-containing amino acids such as cystine and methionine, which are sparingly soluble in water at the isoelectric point. This is because the RO membrane is clogged with the amino acid which separates out upon saturation.

Incidentally, an amino acid is an amphoteric electrolyte which has a carboxyl group (—COOH) and an amino group (—NH$_2$) in the same molecule. Each amino acid has its characteristic constants which are the acid dissociation constants $K_1$ and $K_2$. Therefore, an amino acid dissociates more as the pH of an aqueous solution of the amino acid is adjusted to $pK_1$ or $pK_2$ from the isoelectric point, and the saturation solubility of the amino acid greatly increases in the pH range lower than $pK_1$ or higher than $pK_2$. Amino acids having a low solubility in water as mentioned above are neutral amino acids and the pH of isoelectric point is 5 to 6. Therefore, for example in case of tryptophane ($pK_1=2.3$, $pK_2=9.39$), in order to realize a solubility of 8 to 10 wt. % only by adjustment of pH, the pH must be set in the range of not less than 11 or not more than 2 which is the pH condition deviating extensively from the $pK_1$ and $pK_2$ values. In this way, when the pH is adjusted to the range of less than $pK_1$ of said amino acid or of more than $pK_2$, a large amount of a pH adjusting agent is not only required, but also a pH of the resulting aqueous solution shows a strong acidity or strong alkalinity which deviates from the tolerable pH range of RO membrane, so that there are raised problems in durability of the membrane and in corrosion resistance of a concentration apparatus using the RO membrane Thus, it is, in practice, difficult to increase the solubility of the amino acid by adjustment of a pH only thereby effecting a high concentration through membranes.

Also, there is proposed a method of increasing a saturation solubility by raising temperature thereby effecting a high concentration through membranes. However, there is a limit to the raising of temperature because amino acids are not so good in thermal stability, and the solubility of amino acids is not so temperature-dependent. In case of tryptophan, for instance, the solubility increases by 2% at the best when the solution temperature is raised to 60° C. Thus, the raising of solution temperatures will not provide a high degree of concentration.

Further, most RO membranes of practical use do not withstand temperatures higher than 50° C., although those of heat-resistant type are being developed recently. At high temperatures, they are subject to unreversible deterioration such as change in quality, which shortens the service life.

Thus, the method of increasing the solubility by elevating temperature for concentration through membranes has some problems as mentioned above and therefore, cannot be an effective means for the concentration of amino acids having a low solubility at the isoelectric point and containing hydrophobicity.

SUMMARY OF THE INVENTION

An object of this invention is to provide a process for concentrating highly an aqueous solution of amino acids having a low solubility in water at isoelectric point by means of semipermeable membranes such as reverse osmosis membranes and ultrafiltration membranes (hereinafter referred to as "UF membranes").

The inventors have diligently studied to attain this object and as a result, have found that the amino acid solution having a low solubility in water at isoelectric point can be highly concentrated by means of semipermeable membranes in the presence of a water-soluble organic solvent while increasing the solubility by adjustment of a pH of the solution.

In accordance with this invention, there is provided a process for concentrating an aqueous solution of an amino acid having a low solubility in water at the isoelectric point, which comprises carrying out concentration of said aqueous solution in the presence of a water-soluble organic solvent by means of a semipermeable membrane.

DETAILED DESCRIPTION OF THE INVENTION

Figure 1:
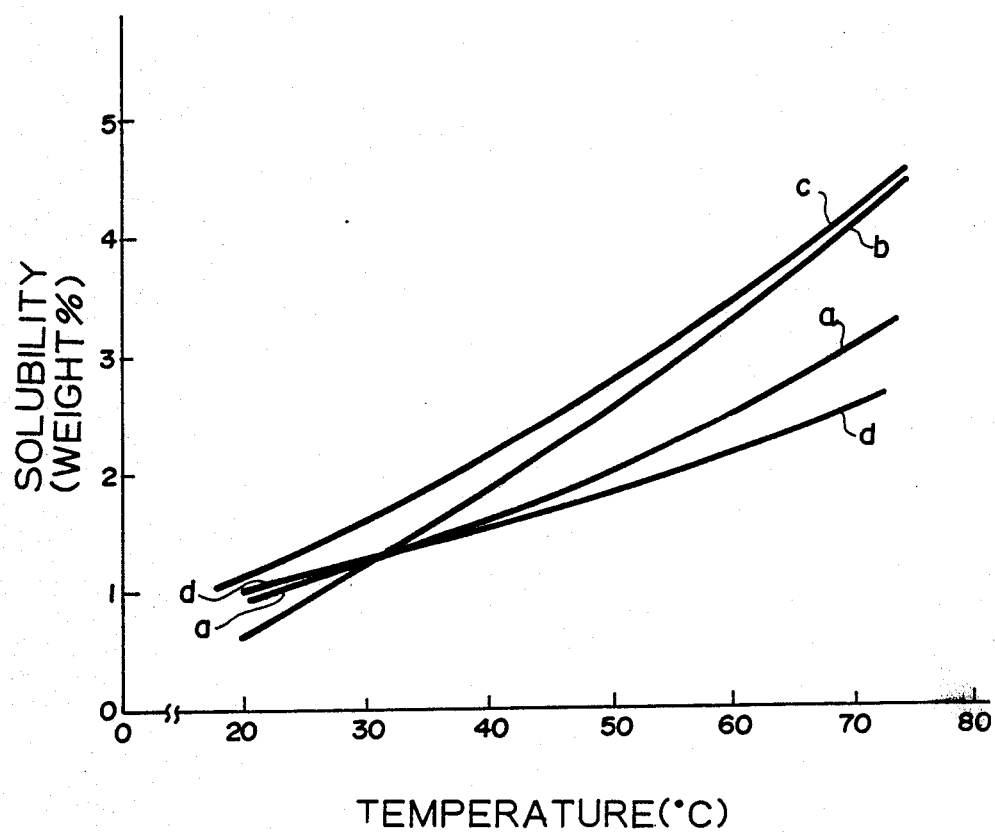
FIG. 1 is a graph showing the temperature dependence of the solubility of L-tryptophan in ethanol-aqueous solutions varying the solvent.

Heretofore, it was almost impossible to concentrate, by using a semipermeable membrane, an aqueous solution of an amino acid having a hydrophobic group such as an aromatic ring in the molecule and hence having a low solubility in water at the isoelectric point. It is known that the concentration is only possible when the solution is heated or the solution is adjusted to a pH in the neighborhood of $pK_1$ or $pK_2$. This is not desirable from the standpoint of the durability of semipermeable membrane and the stability of amino acids. According to the present invention, it is possible to highly concentrate amino acids having a low solubility in water at isoelectric point with a semipermeable membrane without extremely shifting the pH of the aqueous solution from the isoelectric point, simply by adding a proper amount of a water-soluble organic solvent to the aqueous solution. The concentration can be carried out without phase change at almost room temperature. Thus the present invention makes it possible to fully utilize the advantage of a semipermeable membrane at approximately room temperature without bringing about a phase change in the concentration of an amino acid having a hydrophobic group. The process of the present invention is considered to be of great industrial value.

The amino acids to which the method of the present invention is applied are those which are sparingly soluble in water at the isoelectric point. They include amino acids or derivatives thereof having a hydrophobic group such as an aromatic ring or aromatic hetero ring in the molecule, for example tryptophane, tyrosine and phenylalanine. These amino acids having the hydrophobic group have a very low solubility in water because the function of the hydrophilic groups such as carboxyl group and amino group on the side chain is weakened by the hydrophobic group. The presence of the hydrophobic group, on the other hand, renders the amino acid more lipophilic. Because of this lipophilic property, the amino acids having the hydrophobic group increase in solubility when a proper amount of a water-soluble organic solvent such as alcohols is present in their aqueous solution. By contrast, water-soluble aliphatic amino acids such as glycine, alanine, and serine decrease in solubility when alcohol is present in their aqueous solution.

The water-soluble organic solvent to be present in the aqueous solution of amino acid is one which forms a homogeneous phase with water and does not decompose and deteriorate the amino acid in the solution. It should be able to increase the solubility of amino acids with a less amount in the solution, because the osmotic pressure of the solution increases as the amount of the solvent increases in the solution. The osmotic pressure should be low for the passage of a large amount of liquid per unit time and unit area of membrane.

Another requirement for the solvent is that it should not have too many carbon atoms or its substituent should not have too small a Taft number. For these reasons, the preferred solvents are aliphatic lower alcohols, particularly those having 1 to 4 carbon atoms. Examples of such lower alcohols include methanol, ethanol, n-propanol, isopropyl alcohol, and tert-butyl alcohol. The selection should be made on the basis of whether or not the selected one deteriorates or swells the RO membrane or UF membrane used for concentration.

The amount of the solvent to be present in the aqueous solution is not specifically limited. A proper amount should be selected so that the maximum solubility and maximum exclusion ratio of a particular amino acid are attained. It depends on the kind of the amino acid and solvent and the material of the RO membrane or UF membrane used for concentration. It is normally less than 60% by volume, preferably 5 to 50% by volume.

As mentioned above, according to the present invention, it is possible to increase the solubility in water of an amino acid having a hydrophobic group such as an aromatic group, by adding the above-mentioned water-soluble organic solvent to the solution. It is also possible to increase the solubility further by adjusting the solution containing the solvent to a pH above or below the pH of the isoelectric point of the amino acid. The pH to give a desired solubility is not necessarily lower than $pK_1$ or higher than $pK_2$; but it may be closer to the pH of the isoelectric point than in the case where the solution contains no solvent. This is because the solubility has already been increased by the solvent. Needless to say, it is possible to increase the solubility, thereby increasing the degree of concentration, by lowering the pH below $pK_1$ or raising the pH above $pK_2$ so long as the membrane withstands the low or high pH.

The solubility of an amino acid in water can be increased by adding the water-soluble organic solvent to the solution and by adjusting the pH of the solution, as mentioned above. The increased solubility alone is not what is required for effective concentration of an amino acid. The RO membrane or UF membrane used for concentration should be able to stop the passage of as much amino acid as possible and permit the passage of as much liquid as possible.

The RO membrane used for concentration is not specifically limited so long as it withstands the solvent present in the aqueous solution. However, the conventional RO membrane used for desalination is not suitable for the method of this invention, because not only does it have a high exclusion ratio (in excess of 90%) for salt but it also has a high exclusion ratio (in excess of 80%) for the water-soluble solvent disclosed in this invention. This high exclusion ratio results in the concentration of the solvent as well as the amino acid. This concentration causes the aqueous solution to increase in osmotic pressure, which in turn extremely lowers the passage of the liquid and makes it necessary to increase the operating pressure. To avoid this situation and to increase the passage of liquid with a low operating pressure, it is desirable to use an RO membrane which stops the passage of as much amino acid as possible but stops the passage of the solvent to a limited extent. Thus a preferred RO membrane should have an exclusion ratio higher than 80% for the amino acid and an exclusion ratio lower than 50% for the solvent.

The RO membrane having the characteristic properties as specified above is generally called "loose" RO membrane. It includes those RO membranes having an exclusion ratio higher than 90% for common salt in a 1000~5000 ppm aq. solution of common salt at 25° C.

In practice of the present invention, it is more preferable that the exclusion ratio of common salt is not higher than 90% and not lower than 30%. They are commercially available as polyamide composite membrane (NF40HF from Film Tec), aromatic polyamide composite membrane (NF40, NF50, and NF70 from Film Tec), polyvinyl alcohol composite membrane (NTR-7250 from Nitto Denko), polysulfone composite membrane (MRG-5 from Mitsubishi Rayon Engineering), polysulfone composite membrane (U90-G5 from Desalination), and cross-linked polyamide composite membrane (UTC-20 and UTC-40 from Toray). The RO membrane used in the present invention is not limited to them.

In the case of UF membrane, the increase of osmotic pressure by the concentration of the solvent does not take place, because it stops the passage of solutes having higher molecular weight than in the case of RO membrane but it permits the passage of solvent almost freely. On account of its inherent structure, the UF membrane also permits the passage of solutes having a molecular weight close to that of said amino acids. In other words, the UF membrane does not produce the molecular sieve effect for the amino acid, and it does not carry out concentration effectively.

One way to increase the exclusion ratio for said amino acids is to use an UF membrane having fixed positive or negative charges on its surface and to shift the pH of the aqueous solution to be concentrated from the isoelectric point, thereby causing said amino acid to dissociate into acid or base ions, so that the charges on the UF membrane repel the amino acid ions. A positively charged UF membrane is used for an aqueous solution of amino acid which is adjusted to a pH lower than the isoelectric point; and a negatively charged UF membrane is used for an aqueous solution of amino acid which is adjusted to a pH higher than the isoelectric point.

A negatively charged UF membrane is made from polysulfone, polystyrene sulfonic acid, polysaccharide, and the like. A positively charged UF membrane is made from aromatic polyamide or by introducing quaternary ammonium groups in the membrane. The charged UF membrane used for the concentration of said amino acids should preferably be one which is capable of fractionating solutes having a molecular weight lower than 1000.

In case of the RO membrane, although it is not necessarily required to have electric charge on the surface of membrane, it is quite effective to employ electrostatic repulsion between amino acid ions and membrane charge thereby increasing substantially the exclusion ratio of membrane. Thus, needless to say, it is possible to accomplish the high degree of concentration by using a loose RO membrane, if it is charged, the solution contains said solvent, and the solution is adjusted to a pH higher or lower than the isoelectric point according to the charge.

The following examples are illustrative only and should not be construed as limiting the invention.

Referential Example 1:

The solubility of L-tryptophan having an indole ring which is an aromatic hetero ring in an ethanol-aqueous solution was measured at 20° to 75° C. in the usual way. The pH of the aqueous solution was adjusted to the isoelectric point (5.89), and the aqueous solution was prepared from distilled water and reagent grade ethanol. The result is shown in FIG. 1. In FIG. 1, letters a, b, c and d represent the solubility curves of L-tryptophan for the ethanol solution of different compositions shown below.

a: Ethanol: 0 Distilled water: 100 (parts by volume)
b: Ethanol: 30 Distilled water: 70
c: Ethanol: 50 Distilled water: 50
d: Ethanol: 70 Distilled water: 30

It is noted that the solubility of L-tryptophan increases as the temperature goes up from 20° C. to 75° C.

Referential Example 2

Figure 2:
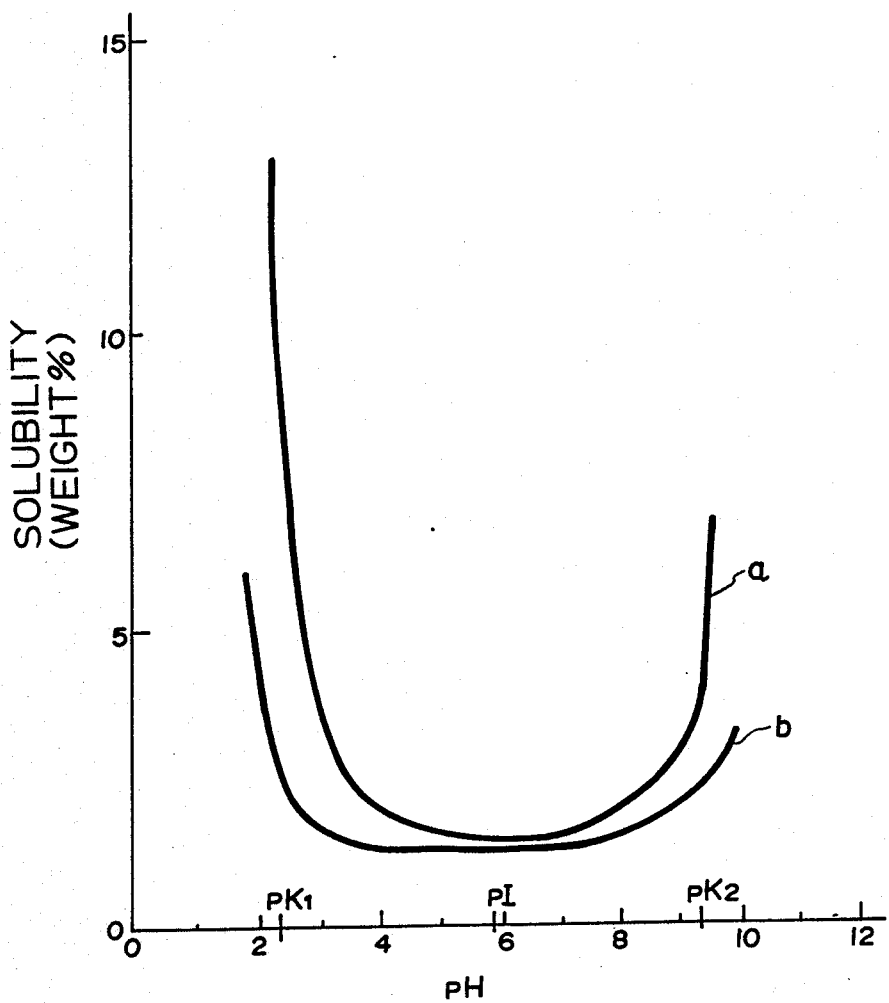
FIG. 2 is a graph showing the pH dependence of the solubility of L-tryptophan in a 50% (by volume) isopropyl alcohol-aqueous solution.

The solubility of L-tryptophan ($pK_1=2.38$, $pK_2=9.39$, $pI=5.89$) toward an aqueous solution of isopropyl alcohol was measured at 40° C. and at pH 2~9.5 in the usual way. The aqueous solution was prepared from distilled water and reagent grade isopropyl alcohol. The pH of the solution was adjusted with reagent grade hydrochloric acid and ammonia water. The result is shown in FIG. 2. In FIG. 2, letters a and b represent the solubility curves of L-tryptophan for the isopropyl alcohol solutions of different compositions shown below.

a: Isopropyl alcohol: 50 Distilled water: 50 (parts by volume)
b: Isopropyl alcohol: 0 Distilled water: 100

EXAMPLE 1

Six liters of an aqueous solution containing 15% by weight of isopropyl alcohol and 1% by weight of L-tryptophan, adjusted to pH 3.0 with reagent grade hydrochloric acid, was subjected to reverse osmosis at 40° C. under 40 kg/cm$^2$ with an aromatic polyamide composite membrane (HR98, a product of DDS). (This membrane is flat and has an effective area of 0.07 m$^2$ and an exclusion ratio of 99.3% for salt in the case of 0.2% saline.) The concentrated solution and the permeated liquid were recycled. The amount of the permeated liquid (per unit area of membrane and per unit time) was 4.1 L/m$^2$·h. The exclusion ratio for L-tryptophan was 98.5%. The exclusion ratio for isopropyl alcohol was 79.0%.

The same procedure as above was repeated with an aromatic polyamide composite membrane (NF40HF, a product of Film Tec). (This membrane is flat and has an effective area of 0.07 m$_2$ and an exclusion ratio of 58.7% for salt in the case of 0.2% saline.) The amount of the permeated liquid was 48.3 l/m$^2$·h. the exclusion ratio for L-tryptophan was 89.7%. The exclusion ratio for isopropyl alcohol was 19.6%.

EXAMPLE 2

Twenty liters of an aqueous solution containing 15% by weight of isopropyl alcohol and 1% by weight of L-tryptophan, adjusted to pH 2.5 with reagent grade hydrochloric acid, was subjected to reverse osmosis for concentration at 40° C. under 40 kg/cm$^2$ with an aromatic polyamide composite membrane (NF40HF, a product of Film Tec). (This membrane is flat and has an effective area of 0.108 m$^2$.) The operation was carried out batchwise for 9 hours. The amount of the concentrated solution (containing 6.0% by weight of L-tryptophan and 21.5% by weight of isopropyl alcohol) was 2.9 liters. The amount of the permeated liquid (containing 0.43% by weight of L-tryptophan and 14.5% by weight of isopropyl alcohol) was 17.1 liters.

EXAMPLE 3

Six liters of an aqueous solution containing 15% by weight of isopropyl alcohol and 1% by weight of L- tryptophan, adjusted to pH 9.5 with reagent grade ammonia water, was subjected to reverse osmosis at 40° C. under 15 kg/cm² with an aromatic polyamide composite membrane (NF70, a product of Film Tec). (This membrane is flat and has an effective area of 0.07 m² and an exclusion ratio of 84.1% for salt in the case of 0.2% saline.) The concentrated solution and the permeated liquid were recycled. The amount of the permeated liquid (per unit area of membrane and per unit time) was 10.4 L/m²·h. The exclusion ratio for L-tryptophan was 90.6%. The exclusion ratio for isopropyl alcohol was 16.0%.

EXAMPLE 4

An aqueous solution containing 20% by weight of isopropyl alcohol and 0.6% by weight of L-tryptophan was adjusted to be a pH of 10.0 by feeding ammonia gas therein and maintained at 40° C. Using a RO membrane spiral module SU-210S (made by Toray Ltd.) composed of a composite membrane of crosslinked polyamide (effective surface area of membrane: 7 m², exclusion ratio for salt at a 1500 ppm aqueous solution of NaCl: 60.5%), 760 of the above aqueous solution was subject to concentration in batch method under conditions of pressure of 30 kg/cm² and temperature of 40° C. After 3 hours, 45 of the concentrated solution (L-tryptophane 6.3% by weight, isopropyl alcohol 22.4% by weight) and 715 of the permeated liquid (L-tryptophane 0.24% by weight, isopropyl alcohol 19.8% by weight) were obtained.

The batch concentration was carried out under the same conditions as the above except not containing isopropyl alcohol in the original aqueous solution. After 2.5 hours from the start of operation, L-tryptophane was deposited in the concentrated solution so that it became impossible to further continue the operation. At this time a concentration of L-tryptophane dissolved in the concentrated solution was 3.8% by weight.

EXAMPLE 5

Using a RO membrane NF40HF (made by Film Tec Company) composed of polyamide composite membrane having positive charge (effective surface area of plane membrane: 0.108 m²), an aqueous solution containing 15% by weight of tert-butyl alcohol and 1% by weight of L-tryptophane (pI=5.89, pK$_1$=2.38, pK$_2$=9.39) was subject to measurement of the exclusion ratio for solute in a wholly circulating method under conditions of pressure of 40 kg/cm² and temperature of 40° C. while varying the pH between 7.3 and 1.8 by means of hydrochloric acid of reagent, special grade.

In case that the pH is 1.8 which is less than pK$_1$ and L-tryptophane is dissociated as almost cations, the exclusion ratio for L-tryptophane was 85.0%. On the other hand, in case that the pH is 5.9 which is approximately isoelectric point and L-tryptophane is hardly dissociated, the exclusion ratio was 69.5%.

What is claimed is:

1. A process for concentrating an aqueous solution of an amino acid having a low solubility in water at the isoelectric point, wherein said amino acid is selected from the group consisting of tryptophan, 5-hydroxytryptophan, tyrosine, phenylalanine, cystine and methionine, which comprises carrying out concentration of said aqueous solution in the presence of an aliphatic alcohol having 1 to 4 carbon membrane by means of a reverse osmosis membrane having an exclusion ratio for NaCl of 30% to 90%.

* * * * *